(12) United States Patent
Ruiz (10) Patent No.: US 6,312,403 B1
(45) Date of Patent: Nov. 6, 2001

(54) EYE DRYER, EYE DRYER SYSTEM AND METHOD OF USING THE SAME

(76) Inventor: Luis Antonio Ruiz, Centro Oftalmólogico Colombiano, Carrera 20 No. 85-11, Pisos 50.-60., Santafé de Bogotá D.C., Colombia (CO)

( * ) Notice: Subject to any disclaimer, the term of this patent is extended or adjusted under 35 U.S.C. 154(b) by 0 days.

(21) Appl. No.: 09/378,692

(22) Filed: Aug. 23, 1999

(51) Int. Cl.[7] .......................... A61M 37/00; A61M 35/00
(52) U.S. Cl. ............................................ 604/23; 604/294
(58) Field of Search .................................. 604/289, 294, 604/295, 296, 297, 298; 606/4

(56) References Cited

U.S. PATENT DOCUMENTS

| | | | |
|---|---|---|---|
| Re. 35,421 | 1/1997 | Ruiz et al. | 606/166 |
| 5,368,590 | 11/1994 | Itoh | 606/4 |
| 5,533,997 | 7/1996 | Ruiz | 606/5 |
| 5,586,980 | 12/1996 | Kremer et al. | 606/4 |
| 5,624,456 | 4/1997 | Hellenkamp | 606/166 |
| 5,658,303 | 8/1997 | Koepnick | 606/166 |
| 5,697,945 | 12/1997 | Kritzinger et al. | 606/161 |
| 5,752,967 | 5/1998 | Kritzinger et al. | 606/166 |
| 5,755,700 | 5/1998 | Kritzinger et al. | 604/257 |
| 5,779,711 | 7/1998 | Kritzinger et al. | 606/107 |
| 5,800,406 | 9/1998 | Kritzinger et al. | 604/257 |
| 5,807,380 | 9/1998 | Dishler | 606/5 |
| 5,817,115 | 10/1998 | Nigam | 606/166 |
| 5,928,129 | 7/1999 | Ruiz | 600/5 |
| 5,954,680 * | 9/1999 | Augustine | 602/42 |
| 6,019,754 * | 2/2000 | Kawesch | 606/4 |

OTHER PUBLICATIONS

Surgery for Hyperopia and Presbyopia, Neal A. Sher, MD, FACS, pp. 121.

* cited by examiner

Primary Examiner—Kim M. Lewis
(74) Attorney, Agent, or Firm—Smith, Gambrell & Russell, LLP (57) ABSTRACT

An eye dryer device has a main body that includes a chamber which receives gas from an external source through an inlet port formed in the main body. The main body includes a lower shell section that has a plurality of exit ports such as 25 to 125 exit ports of relatively small size such as 0.5 mm to 2 mm which are arranged above the eye for providing a gentle, highly dispersed plurality of gas streams well suited for quickly drying a flap or cap of an eye following repositioning in a laser surgery (LASIK) procedure. The main body features an outer cover section which is joined such as by way of an adhesive with the lower or inner shell section about their common periphery or integrally joined such as by way of a common hardened melt region or an initial monolithic formation. The chamber is positioned between the inner shell section and outer cover section with each preferably having a convex-shape with a generally oval-shaped periphery for sealing position over an eye. A system is provided that includes the eye dryer together with a source of clean (filtered) gas, a gas communication line and a handle with an internal gas passageway which is received preferably by way of a friction plug-in receptor secured to the eye dryer and in gas communication with the inlet port leading into the chamber. A line on/off valve is provided to allow a surgeon to control the onset and conclusion of eye drying gas which typically only involves less than a half of a minute and often 20 seconds with the arrangement of the above described eye dryer.

28 Claims, 5 Drawing Sheets

EYE DRYER, EYE DRYER SYSTEM AND METHOD OF USING THE SAME

FIELD OF THE INVENTION

The present invention relates to an eye dryer, an eye dryer system and a method of using the same. The present invention has particular utility in drying an eye following corneal flap or cap repositioning as part of a Laser Assisted In Situ Keratomileusis (LASIK) procedure or the like.

BACKGROUND OF THE INVENTION

Corneal surgery to supplement or replace the need for optical aides (e.g., eyeglasses and contact lens) or to treat eye conditions has undergone a steady evolution over the last 50 years or so. Advancements in the field has resulted in even greater attention being given to ways in improving the safety and results of the various techniques involved. This evolution has included the replacement of diamond blade incision techniques such as Radial Keratatomy (RK) and its related procedures of Astigmatic Keratatomy (AK) and Hexagonal Keratotomy (HK) with excimer laser techniques such as Photorefractive Keratectomy (PRK) and Laser Assisted In Situ Keratomileusis (LASIK). The excimer laser can be extremely accurate and removes only small amounts of eye tissue per pulse (e.g., 0.25 microns or 1/4000th of a millimeter). During the resculpturing or other desired effect on the eye, the laser is relied upon to gently "evaporate" tissue through an ablation process on the above noted small amount of eye tissue. In most cases the laser treatment only lasts 20 to 45 seconds depending upon the severity of the refractive error.

As described, for example, in U.S. Pat. No. 5,368,590, in PRK the laser is applied directly to the surface of the cornea, after the thin surface layer of cells or epithelium is removed, to re-shape the cornea to make the resultant curve of the cornea balance the length of the eye in an effort to have the light rays better focus on the retina. Phototherapeutic keratectomy, such as corneal leukoma, pterygium, corneal erosion, and herpetic keratitis surgeries are also described in U.S. Pat. No. 5,368,590 as being suited for laser use. In the PRK procedure, a lid retractor is put into position so as secure the eye lid open so as not to interfere with subsequent treatment steps. The positioning of the retractor leads to the exudation being exuded onto the corneal surface. As described in U.S. Pat. No. 5,368,590 such exudation is eliminated by manually applying a conventional sponge, stick type absorbent, or gauze and/or a drainage tube. The elimination of the exuded liquid is described as being important as the exuded fluid is said to be a source of treatment error due to the liquids disruption of the desired ablation effect on eye tissue. In the noted patent, there is indicated that the prior art techniques fail to maintain a dry eye during sudden releases of large amounts of fluid and describes a large, encompassing corneal sponge designed to provide at least one dry, surgical space. Thus, the '590 reference relies on a peripheral absorption technique to help avoid build up in the treatment area of the eye by drawing the fluid away from that area.

PRK has, however, been generally replaced by the "LASIK" method in which the laser treatment is applied under a corneal flap. This avoids many of the problems often associated with PRK such as the degree of uncomfortableness, correction regression, potential scarring, hazing, unpredictability, etc. which come about, mainly due to the treatment of the regenerative outer layer of the eye during PRK. This is not the case with LASIK as the laser treatment is directed toward reshaping the cornea stroma which does not create the same problems that arise in a PRK procedure. The flap replacement in LASIK also covers the treated area avoiding treatment area exposure which is a main cause of discomfort and potential infection in PRK.

To produce the corneal flap, a portion of the cornea is resected to expose the corneal stroma. U.S. Pat. No. Re. 35,421 to the present inventor, Dr. Luis A. Ruiz, and Sergio Lenchig, which patent is incorporated herein by reference, describes an automated corneal shaper that is well suited for providing the eye resection. The automated corneal shaper provides for a resection in the form of a flap (a hinged resection) for facilitating repositioning or the resection after the exposed surface is subjected to laser treatment. The automatic corneal shaper noted above provides a means for automatically, precisely and safely performing corneal resections for refractive corrections such as hyperopia, myopia, astigmatism, and/or the correction of presbyopia (as described in Dr. Ruiz's U.S. Pat. Nos. 5,533,997 and 5,928, 129 each of which is incorporated by reference) and other eye correction techniques where a lamellar resection is desired (e.g., keratomileusis).

In view of the above-noted advantages of LASIK, LASIK surgery has become the standard for refractive surgery, providing excellent results in terms of accuracy, safety, short recovery time and a minimum of post operative symptoms. As described in U.S. Pat. No. 5,755,700 to Kritzinger (which reference is incorporated herein by reference), while a great deal of focus has been on what type of ablation to use in the bed, other areas which warrant attention are safe keratectomy and accurate repositioning of the cap/flap. The above described automatic corneal shaper is directed at the first of the noted concerns. As to the accurate repositioning, the prior art teaches a variety of markers to help in the final repositioning of the flap. An example of one such marker is seen in U.S. Pat. No. 5,752,967 to Kritzinger et al.

As a marker only helps in providing repositioning guidance, it does not provide a solution to the other potential complications associated with flap replacement during LASIK surgery. After the laser portion of LASIK treatment (which often takes place in well under 30 seconds) it is desirable to quickly place the flap or cap back in position from the standpoint of, for example, avoiding prolonged exposure of the corneal stroma and avoiding a large differential between the actual surgical time and the time a patient has to wait before the equipment around the eye can be removed. However, a too hasty replacement can lead to wrinkling or folding of the flap or cap, which, due to the high liquid surface adhesion along the overlapped region, can lead to inadvertent tearing or stretching when attempting to remove folds or wrinkles or in the lifting off of the flap from the corneal stroma for a second attempt at placement.

Also even if the flap is initially positioned properly (e.g., without wrinkles or folds), the conventional drying techniques can introduce wrinkles, folds and non-alignment problems during the course of drying. For instance if the eye is dried by way of a conventional technique such as applying drying air through the end of a conduit with or without an added nozzle end, the force of the applied air (or other gas) stream to the eye can create shifting, wrinkling and folding in the flap. That is, excessive drying can cause wrinkle formation while defective drying can cause inadvertent flap replacement. While the flap can be dried without the assistance of applied air or gas, the time involved for atmospheric drying is undesirable in that it involves a drying time period that is many times the length of time involved for laser application, and requires the patient to remain under the surgical setting for an undesirable long period of time.

There is also know in the art clear plastic "bubble" eye shields with through holes, which shields are used post operatively to protect the eye from trauma. An illustration of one such bubble shield is found on page 121 of "Surgery For Hyperopia and Presbyopia" by Neal Sher, MD, FACS. This device is far removed from an eye drying device.

SUMMARY OF THE INVENTION

The present invention is directed at greatly reducing the drying time, while avoiding problems such as defective, excessive or inadequate drying. The invention features an airflow chamber which, due to the air movement inside the chamber and out from the chamber, reduces the drying time from a typical conventional period of about 4 to 7 minutes to less than a minute, generally less than 30 seconds and more typically about 20 seconds in a typical setting. That is, with the present invention the same dryness level can be achieved in less than a minute as compared to the 4 to 7 minutes common with the other conventional drying techniques.

In utilizing the present eye drying system, an eye ablation is finished, and the flap is placed back in its original position (preferably with the assistance of markers), a check is made of the flap's borders with the merocel sponge to insure the symmetry. Then the dryer is placed over the eye for at or about 20 seconds. At the end of this time the dryer is removed as well as the speculum. A check is then made for proper flap adherence with manual movement of the eyelid. A proper drying procedure is considered one wherein there is lacking any wrinkles or folds in the replaced flaps and there is no displacement due to the manual eye movement.

In a preferred embodiment, the chamber is made up of two clear plastic shields, the lower one with holes to allow a uniform and highly dispersed air flow, the upper one representing a sealed cover. There is a cavity between the shields that is connected to the air source and a handle connected to the interconnected seals through which the air preferably flows through before entering the chamber.

In the presence of a free cap (as opposed to a flap), once the cap is clean and replaced on the bed, the only difference in the drying technique is that now the entire placement and drying process will take a little longer (e.g., between 60 an 90 seconds). That is, with the present invention the drying time is typically about 20 seconds, and there is typically involved another 40 to 70 seconds in proper positioning of a cap. With a flap, however, the repositioning time is lessened (e.g., one half the repositioning time that is required for cap repositioning).

DETAILED DESCRIPTION OF THE INVENTION

Figure 1:
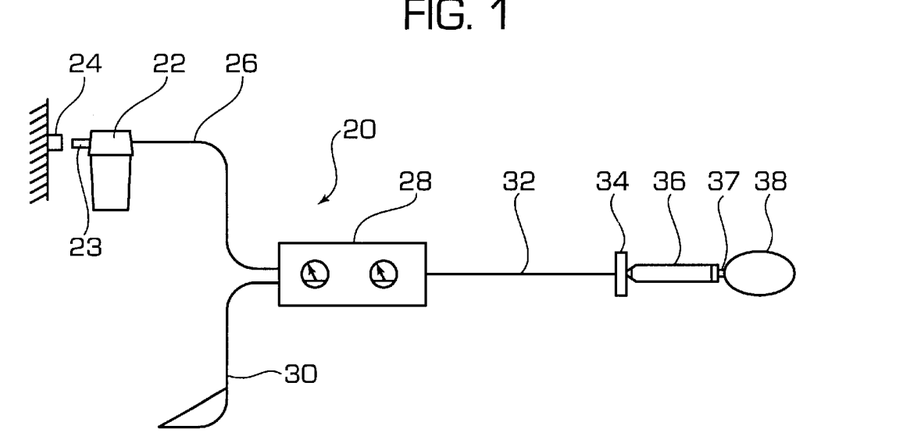
FIG. 1 illustrates a schematic representation of an eye drying system of the present invention.

FIG. 1 shows a schematic representation of an embodiment of eye dryer system 20 of the present invention which includes air filter 22 with attachment 23 for connection with wall air outlet 24 of a general air supply system (not shown) with the output typically set at 100 psi. Flexible hose 26 (preferably a flexible ¼ inch plastic hose) extends from air filter 22 to interface console 28. Interface console 28 provides a step-down of pressure from 100 psi to 25 psi and regulates the air flow to a preferred flow volume of about 10 liters/min. Foot switch 30 allows the surgeon to turn on and off the air flow (e.g., foot depression allowing for the through flow of air through and past interface console 28). The air exiting console 28 travels along flexible conduit 32 (preferably a ⅛th inch plastic tube) until reaching smaller or micro pore filter 34 such as a VISITEC 1030 (TM) high flow 0.2 micron filter. Downstream of filter 34 is handle 36 which also includes means for attaching to eye dryer 38 at its downstream end such as a friction plug-in arrangement and an internal passageway which provides for uninterrupted air flow through the handle.

Figure 2:
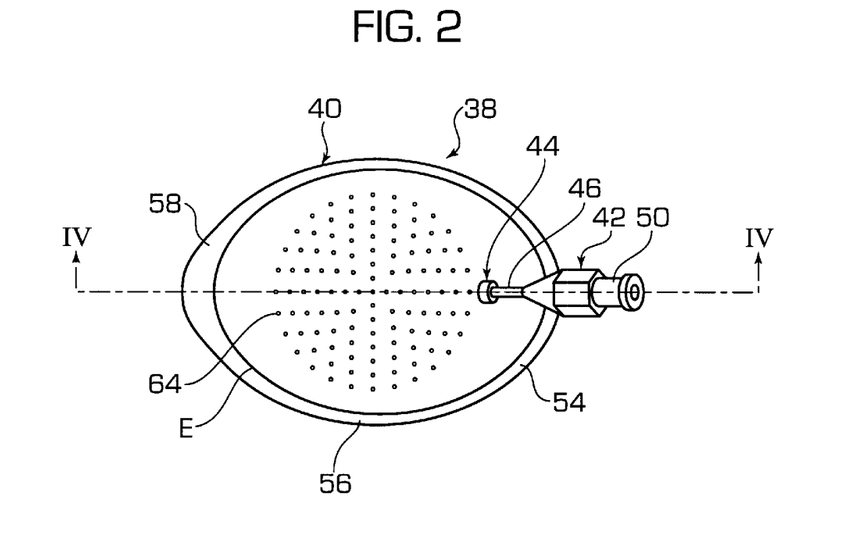
FIG. 2 illustrates a top plan view of an eye dryer or air flow chamber device of the present invention.
Figure 3:
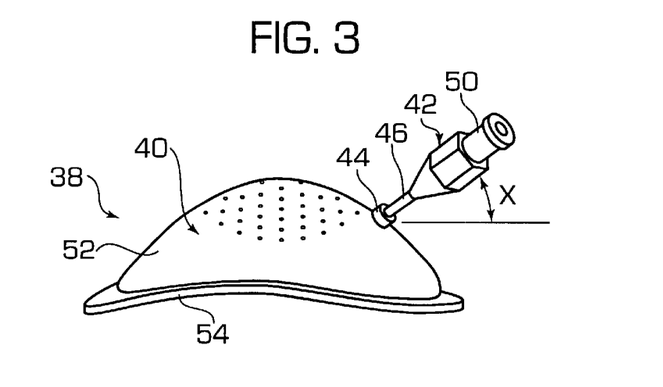
FIG. 3 illustrates a side elevational view of that which is shown in FIG. 2.
Figure 4:
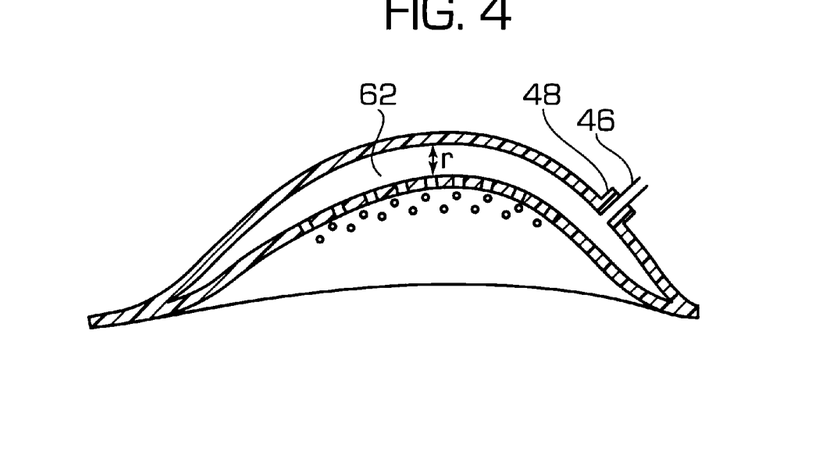
FIG. 4 illustrates a cross-sectional view taken along IV—IV in FIG. 2.

FIGS. 2 and 3 illustrate in greater detail eye dryer 38 which comprises airflow chamber device 40 and port connector 42. Port connector 42 preferably includes seal 44 to facilitate the providing of an air tight seal between the exit end 48 (FIG. 4) of injection conduit 46 of port connector 42 and chamber device 40. The inlet end of port connector 42 includes plug-in reception member 50 which receives the downstream connecting end of handle 36 (FIG. 5) in a gas tight relationship. Port connector 42 includes a central air passageway which extends continuously through port connector 42 and out of exit end 48 (FIG. 4) to air flow chamber 40 (FIG. 2) as explained in greater detail below.

Air flow chamber device 40 is preferably formed of an inner shell and outer shell which are connected or formed originally as a monolithic unit (e.g., connection by way of an adhesive or heat bonding or formed as a one piece monolithic member through blow molding or the like). Air flow chamber device 40 is also preferably formed entirely of a transparent or translucent plastic such that the surgeon can see through to the eye being dried. As best shown is FIG. 4 and 6 air chamber device 40 includes outer or external shell 52 (FIG. 6) which is continuous or uninterrupted except for opening 54 through which either the exit end 48 of port connector 42 alone or both the seal 44 and exit end of port connector 42 (a stepped shoulder seal arrangement) extend.

Outer shell 52 is generally convex in shape having a maximum height H preferably from 15 to 30 mm, more preferably 18 mm to 22 mm with 20 mm being highly preferred. Height H is measured from base B which is a generally horizontal plane lying flush with the lowest most ends (lying generally along cross-section line IV—IV) of the lower edge E of shell 52.

Figure 6:
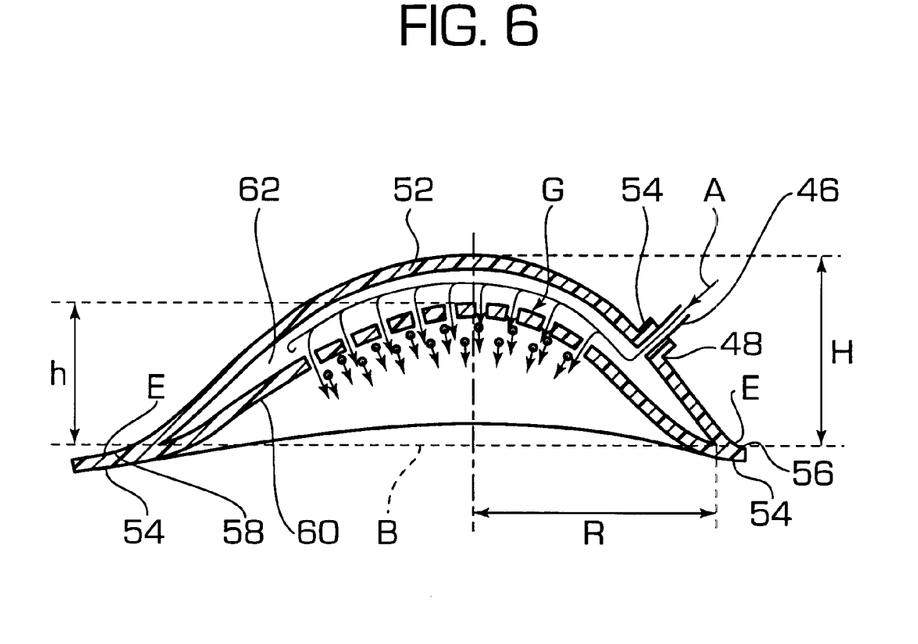
FIG. 6 shows a view similar to that of FIG. 4 with an added schematic representation of the drying gas flow with respect to a preferred embodiment of an eye dryer of the present invention.

As shown in FIGS. 2, 3 and 6, for example, flange 54 extends peripherally outward and continuously about the generally oblong edge E (FIG. 6). Flange 54 has a smaller width section 56 which extends essentially continuously about almost the entire periphery of edge E. Enlarged flange section 58 is provided at the opposite end to the end where port connector 42 is received. Enlarged flange section 58 slopes downward and outward as shown in FIG. 6 to help better conform to the reception area on the patient. Similarly, the curvature variation of the bottom surface of flange 54 with respect to the vertical is designed to conform to the surface about the patient's eye (in the eye socket region) such that a seal can be formed between the flange 54 and the enlarged flange section 58 with respect to the patient's skin surface about the eye with a low level (i.e., not uncomfortable) pressure application. Enlarged flange section 58 also helps in facilitating proper positioning of air chamber 40 device with respect to the eye as it nestles within the eye cavity on the nasal side. It also provides a convenient grasping location. A compressible foam or elastomeric seal can also be provided along the undersurface of flange 54, but the combination of the flange configuration shown in the figures and the compressible nature of the skin in the area bordering and also within a person's eye socket has shown to be sufficient for the purposes of the present invention. To provide a generally universal size for most patients (particularly adult patients) the flange 54 has a generally oblong or oval peripheral shape with a major diameter of 6.5 cm, when including enlarged flange section 58, or about 6.0 when the enlarged flange section 58 is excluded resulting in major radius R in FIG. 6 being equal to 3.0 cm. With this major diameter size a minor diameter of about 5.0 cm is preferred. These dimensions are representative of a preferred embodiment suitable for a wide variety of patients. The providing of alternate size eye dryers is also in accordance with the present invention such as a scaled down eye dryer for small infants.

As shown in FIG. 6, second, internal shell 60 also has a convex shape that generally conforms to that of outer shell 52 except its height h (from base B to the maximum upper point on inner or lower shell 60) is less than that of upper shell 52 so as to form cavity or chamber 62 between the two shells. The maximum height of cavity or chamber 62 is shown in clearer fashion in FIG. 4 and is represented by r with r=H−(h+t) with "t" being the thickness of the outer shell (and also preferably the inner shell). A preferred range of maximum chamber height "r" (FIG. 4) is 0.5 to 5 mm, more preferably 0.5 to 2 mm, with 2 mm being a highly preferred height which can be provided by having H=20 mm, h=16.5 mm and t=1.5 mm. With the thickness of each shell being preferably the same, the cavity formed by the cup-shaped inner shell above the eye thus has a maximum height of 15.0 mm. The height or thickness (taken along a line that is transverse to a tangent sharing a common point on the curved surface of the outer shell 52) of chamber 62 does not appreciably vary from the maximum height (e.g. less than 10–20%) in the central region of the eye dryer, but reduces in going toward the common boundary edge E wherein upper and lower shells 52 and 60 merge. (e.g., a 60 to 80% generally common chamber height r followed by a gradual reduction to contact for the corresponding range of 40 to 20% of the chamber area).

Lower shell 60 features a plurality of through-holes which represent air or gas chamber exit ports 64. Ports 64 are arranged along (and through) the convex lower shell and preferably feature a large number of smaller holes (e.g., 25–150 holes of about 0.5 to 5 mm with about 100 to 125 at about 0.5 to 2 mm being preferred, and even more preferably 100 to 125 holes at 1 to 2 mm) so as to provide a large number of small diameter air or gas streams that at least fully encompass the flap area and also extend out from that area. For example, keratomes typically have a resection formation range of about 4–9 mm, and the preferred value for the length of coverage along the nasal or "N-T" axis is at least two times the maximum flap diameter along that axis and more preferably about three to ten times that maximum (e.g. a 3 cm to 4 cm length for the port coverage area with about 3.5 cm being preferred; which 3.5 cm length would be about four times a flap section of 9 mm). The flap is also preferably centered with respect to the overlying pattern or area of outlet port 64 coverage which coverage area is generally designated as "G". In this way the flap, flap border and the external surrounding region are covered by the outlet ports coverage region G. A similar distance or length of coverage is also involved along the Superior/Inferior axis or S-I axis. This results in a generally circular region G for ports 64, although an oblong or oval shape is also well suited for the purpose of the present invention. For example, an N-T axis coverage distance 5 to 15% greater than the S-I axis distance (the minor axis of the oval shape) for the coverage area G would also be well suited for providing rapid drying.

Figure 9:
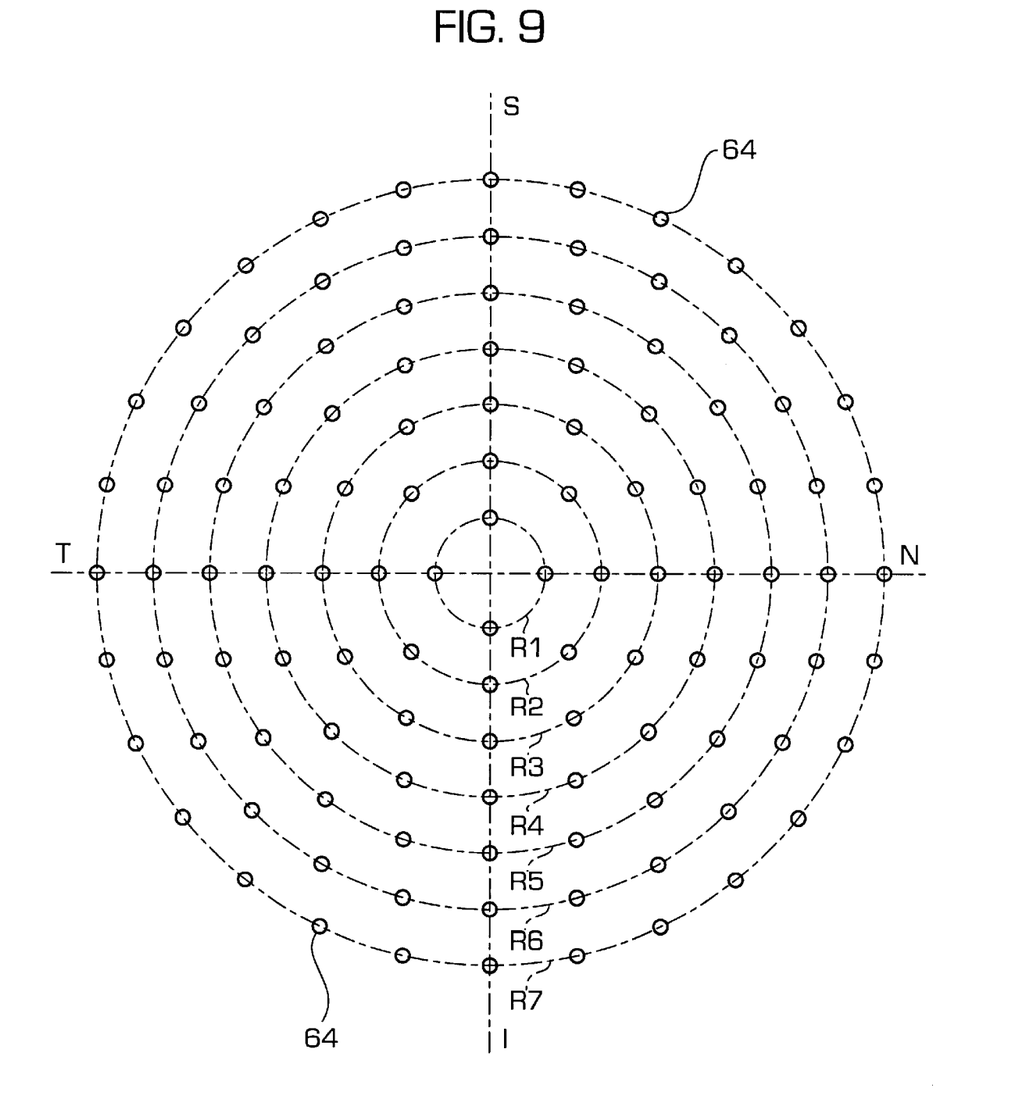
FIG. 9 shows an example of a preferred air port pattern.

Preferably the through-holes are spaced in a pattern to help promote generally equal application of the air flow exiting ports 64 to promote equal drying across the eye flap and surrounding area. Preferably the ports have a diameter within 0.5 mm to 5 mm, a preferred value is 1 mm diameter for each through-hole. While a plurality of specific patterns (as well as random port positioning) and a variety of sizes are possible, FIG. 9 illustrates one preferred pattern for the through-holes or ports 64 that helps promote rapid and effective drying. This pattern features groups of ports arranged on concentric rings with each group having equally circumferentially spaced ports with the number in each group expanding together with the increase in circumferential diameter. For example, FIG. 9 shows a preferred pattern comprised of seven rings (R1–R7) with each ring being spaced from about 2 to 4 mm apart and each ring containing ports of about 1 mm in diameter. The number of ports on each ring preferably follows the number pattern 4-8-12-16-20-28-32 which has shown to provide efficient drying performance through a gentle, well dispersed application of the gas flowing through the ports 64 following gas passage through the handle and into chamber 62. While the illustrated pattern in FIG. 9 for application to the curved interior shell wall is preferred, other patterns that provide the gentle, well dispersed gas application to the relevant area, which includes the flap, the flap border region and the portion of the eye external to the flap, are also possible (e.g., a spiral pattern extending out from a centralized port).

As shown in FIGS. 2 and 3, port connector 42 is arranged along the central cross section line IV—IV extending along the N-T axis of the eye-shaped (general oval shape) airflow chamber device 40. Cross section line IV—IV also extends through the center of enlarged flange section 58. Enlarged flange section 58 is positioned on the opposite side of airflow chamber device 40 as compared to port connector 42. This arrangement provides for easy manipulation of airflow chamber device 40 once connected to handle 46 as the connected handle 36 extends out away from the operation area along the N-T axis. This positioning also avoids visual interference and physical interference with respect to the retractor and surgical drape and other surgical components. FIG. 3 also shows port connector 42 extending out at an angle "X", which in a preferred embodiment is 30–60° and more preferably about 45°. This orientation provides easy handle plug-in access and also facilitates maintaining handle 36 in a non-interfering position.

Figure 5:
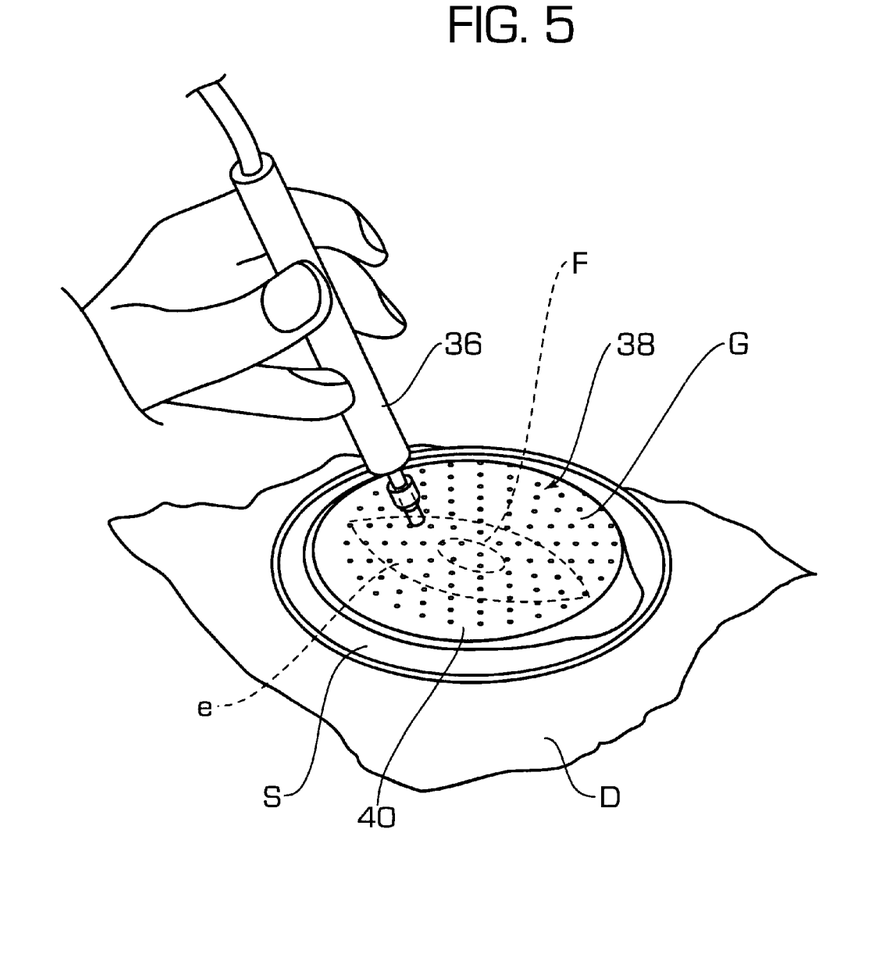
FIG. 5 illustrates an eye dryer applied to an eye.

FIG. 5 shows eye dryer 38 in operative position over eye "e" with port coverage area G positioned above and centered with respect to flap F. Surgical drape D extends about eye C with a narrow region of exposed eye socket region S therebetween.

FIG. 6 illustrates air flow A entering into chamber 62 from injection end 48 of conduit 46. As shown, the outer periphery of port coverage area G is radially inward of outlet 48 so that the air flow is not fed directly into one or more ports 64, but instead is reflected off the internal surface of inner shell 60 for greater dispersion within chamber 62. The volume of chamber 62 is also sufficiently large relative to the size of the outlet ports 64 such that full chamber dispersion of the air flow, and generally equal outflow of the air through ports 64, is possible. Because the diameter of ports 64 is relatively small (e.g., 1–3 mm) a finely dispersed air drying flow is applied to the flap, flap border and surrounding region which achieves the rapid drying (e.g., less than one minute) described above.

Figure 7A:
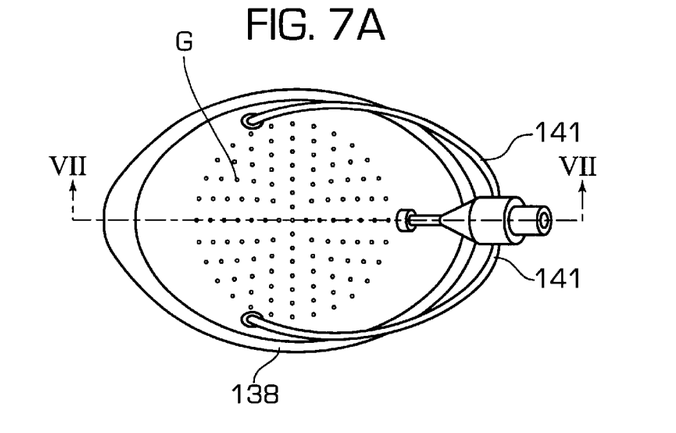
FIG. 7A illustrates a top plan view of a modified embodiment of the eye dryer of the present invention.
Figure 7B:
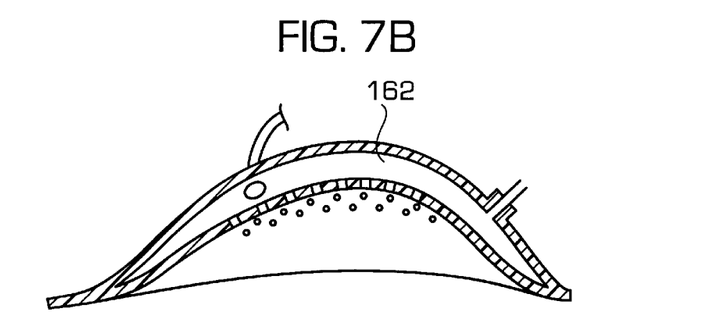
FIG. 7B shows a cross-sectional view taken along cross-section line VII—VII in FIG. 7A.

FIGS. 7A and 7B illustrate an alternate dye dryer embodiment 138 which features a manifold arrangement 141 which includes a plurality of clear plastic branch conduits 140, 142 which are arranged to help promote a high degree of initial dispersion of the incoming air flow into chamber 162. From the standpoint of avoiding complexity and avoiding visual disruptions the first embodiment is preferred, although the increased dispersion can facilitate a more equal application of gas application in the desired drying area.

Figure 8A:
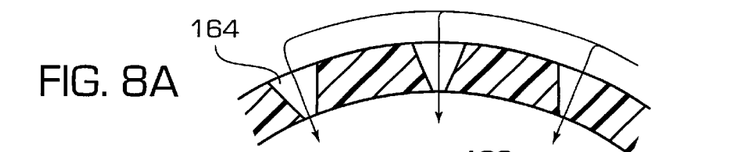
FIGS. 8A to 8C show various alternate gas flow ports for the eye dryer.
Figure 8B:
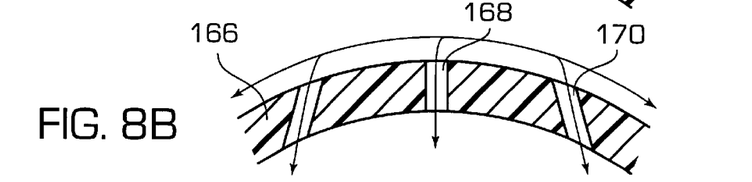
Figure 8C:
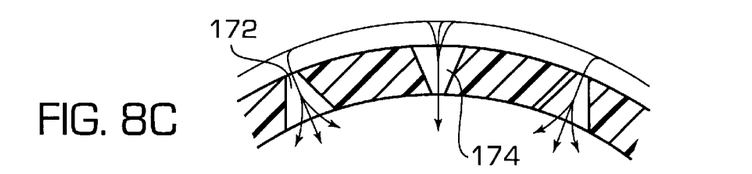

FIGS. 8A, 8B and 8C illustrate some alternate embodiments for ports being formed in the inner shell of the eye dryer device. In FIG. 8A, ports 164 are conical in shape to promote a velocity increase in each individual air channel in passing through ports. This is one illustration of altering the port configuration to alter the characteristics of the air streams exiting the ports and/or to provide for upstream variations in features such as the pressure of the air stream being directed to the handle or the volume or configuration of the reception chamber between the shells.

FIG. 8B is illustrative of providing a variety of differently oriented port air flow axis for ports 168, 170 and 172 which provide greater versatility in the make-up of the air flow to be applied to the closed flap For example, a more transversely arranged port such as 168 is shown positioned in a central area of the flap where there is not a great a risk of flap lift up, while further out on the inner shell where the air flow is directed at the flap boundary with suitable angling the maintenance of a non-lift, smoothing air flow is possible. This type of arrangement expands the possibilities for increased port sizes and/or upstream pressure and corresponding air stream velocities. Although not shown, a variety of different size ports may be relied upon preferably with the number within a particular sub-region of region G being designed for the intended purpose (e.g., a greater flow volume in a direct central region as compared to a peripheral region or a greater volume external to the border region to preclude built up extruded fluid from re-wetting the flap to an undesirable degree—note the non-uniform step increase in the number of ports in the outer two rings of FIG. 9).

FIG. 8C is illustrative of an alternate embodiment wherein a combination of more dispersive type ports 172 are strategically located (e.g., in the flap boundary region) while less dispersive port shapes are provided at a different location such as a more centralized location.

From the standpoint of, for example, ease of manufacturing, particularly when using the preferred large number (e.g., 120 ports) of small diameter ports (e.g., 1 mm) the embodiment illustrated in FIG. 2 is preferred.

Although the present invention has been described with reference to preferred embodiments, the invention is not limited to the details thereof. Various substitutions and modifications will occur to those of ordinary skill in the art, and all such substitutions and modifications are intended to fall within the spirit and scope of the invention as defined in the appended claims

What is claimed is:

1. An eye dryer device, comprising:
   a main body that includes a chamber formed therein, said main body further including an inlet port for receiving a gas flow from an external source, and said main body further comprising a plurality of exit ports; wherein the main body is designed to conform to the surface about the eye.

2. The eye dryer as recited in claim 1 wherein said main body comprises an outer cover section and an inner section which are in contact, and said chamber being positioned between, said inner section and outer cover section, and said inner section having said exit ports.

3. The eye dryer as recited in claim 2 wherein said inner section is a generally convex shaped shell defining an interior cup region and wherein said plurality of exit ports have a diameter that is smaller than said inlet port.

4. The eye dryer as recited in claim 3 wherein said outer cover section is a generally convex shaped shell which shares a common border region with said inner section and has an internal surface spaced from an internal surface of said inner section so as to define said chamber therebetween.

5. The eye dryer as recited in claim 4 wherein said inlet port is formed in said outer cover section, and said inlet port is arranged such that the gas flow first strikes against a portion of the internal surface of said inner section which is free of exit ports.

6. The eye dryer as recited in claim 4 further comprising a port connector which extends external to said main body and includes an internal gas passageway which opens and opens into said chamber.

7. An eye drying device as claimed in claim 2, wherein said outer cover is formed of a monolithic material which is self sustaining in shape.

8. The eye dryer as recited in claim 1 further comprising a port connector which extends external to said main body and includes an internal gas passageway which opens into said chamber.

9. The eye dryer as recited in claim 8 wherein said port connector includes a receptor for receiving a gas supply member.

10. The eye dryer as recited in claim 9 wherein said receptor includes a friction reception recess for receiving in plug in fashion the gas supply member.

11. The eye dryer as recited in claim 1 wherein said main body is a monolithic body.

12. The eye dryer as recited in claim 11 wherein said monolithic body is a transparent or translucent main body.

13. The eye dryer as recited in claim 1 wherein there are at least 25 exit ports of a diameter smaller than said inlet port.

14. The eye dryer as recited in claim 13 wherein the diameter of said exit ports is between 0.5 mm to 5 mm.

15. The eye dryer as recited in claim 13 wherein there are at least 100 exit ports having a diameter between 0.5 mm to 3 mm.

16. The eye dryer as recited in claim 1 wherein said main body includes a cup shape and has a lower rim shaped for conforming to the contour about a person's eye.

17. A method of drying an eye comprising:
   placing the eye dryer device of claim 1 about a person's eye; and
   directing gas to the inlet port and exit ports onto the person's eye; thereby drying the eye.

18. The method of claim 17 wherein there are at least 25 exit ports through which the gas flows.

19. An eye drying system, comprising:

the eye dryer of claim 1; and a gas line, said gas line being in gas communication with said inlet port, and said exit ports exiting into a cup shaped region defined by said main body and dimensioned for positioning over an eye of a patient.

20. The eye drying system as recited in claim 19 wherein said eye dryer includes an outer shell section having a generally convex shape, and an internal shell section having a convex shape and an interconnected or mutual region with respect to said outer shell section, and said inner and outer shell sections being spaced apart along a portion thereof so as to define the chamber in communication with said exit ports and said inlet port.

21. The eye drying system as recited in claim 19 further comprising a gas filter which receives gas flowing within the gas line and is positioned upstream, with respect to gas flow, of said eye dryer.

22. The eye drying system as recited in claims 21 wherein said filter is a micropore filter.

23. The eye drying system as recited in claim 19 further comprising a gas interface console in gas flow communication with respect to gas traveling in said gas line.

24. An eye drying system comprising:

the eye dryer of claim 1, wherein said exit ports exit into a cup shaped region defined by said main body and dimensioned for positioning over an eye of a patient;

a gas line, said gas line being in gas communication with said inlet port; and a handle in gas communication with said gas line.

25. The eye drying system as recited in claim 24 further comprising a reception member secured to said main body and having a reception port designed for sealing connection with a gas exit end of said handle.

26. A method of drying an eye, comprising:

directing gas to an inlet conduit of an eye dryer, said eye dryer having an inlet port for receiving directed gas and a plurality of exit ports which exit into a cup-shaped region of a main body of the eye dryer which main body has a contact edge designed for contact about an eye of a patient being dried.

27. The method of drying an eye as recited in claim 26 wherein there are at least 25 exit ports through which gas directed into said chamber flows through.

28. An eye dryer device, comprising:

a main body that is formed of a monolithic material which is self sustaining in shape and includes a chamber formed therein, said main body further including an inlet port for receiving a gas flow from an external source, and said main body further comprising a plurality of exit ports which are positioned with respect to said main body to direct a drying gas to an eye being dried, and wherein the eye dryer device is designed to conform to the surface about the eye.

* * * * *